(12) United States Patent
Langer

(10) Patent No.: US 12,295,570 B2
(45) Date of Patent: May 13, 2025

(54) SURGICAL TOOL AND SURGICAL SET

(71) Applicant: Medartis Holding AG, Basel (CH)

(72) Inventor: Barry Langer, Therwil (CH)

(73) Assignee: Medartis Holding AG, Basel (CH)

( * ) Notice: Subject to any disclaimer, the term of this patent is extended or adjusted under 35 U.S.C. 154(b) by 542 days.

(21) Appl. No.: 17/622,107

(22) PCT Filed: Jun. 25, 2020

(86) PCT No.: PCT/EP2020/067857
§ 371 (c)(1),
(2) Date: Dec. 22, 2021

(87) PCT Pub. No.: WO2020/260470
PCT Pub. Date: Dec. 30, 2020

(65) Prior Publication Data
US 2022/0240931 A1     Aug. 4, 2022

(30) Foreign Application Priority Data

Jun. 28, 2019  (EP) .................................. 19183164

(51) Int. Cl.
*A61B 17/064*  (2006.01)
*A61B 17/00*  (2006.01)
(Continued)

(52) U.S. Cl.
CPC ........ *A61B 17/0642* (2013.01); *A61B 17/105* (2013.01); *A61B 17/17* (2013.01);
(Continued)

(58) Field of Classification Search
CPC ... A61B 17/0642; A61B 90/03; A61B 17/105; A61B 17/17; A61B 2090/037; A61B 2017/00526
See application file for complete search history.

(56) References Cited

U.S. PATENT DOCUMENTS

| 4,641,648 A | * | 2/1987 | Shapiro .................. A61B 90/00 623/7 |
| 5,080,275 A | * | 1/1992 | Heimerl ............. A61B 17/0684 227/176.1 |

(Continued)

FOREIGN PATENT DOCUMENTS

| CN | 103302682 A | 9/2013 |
| DE | 19859950 C2 | 3/2000 |

(Continued)

OTHER PUBLICATIONS

International Search Report for International Application No. PCT/EP2020/067857 mailed Sep. 29, 2020, 3 pages.

(Continued)

*Primary Examiner* — Kevin T Truong
*Assistant Examiner* — Diana Jones
(74) *Attorney, Agent, or Firm* — Finch & Maloney PLLC

(57) ABSTRACT

Disclosed are surgical tools (10) comprising a surgical clamp (20) having at least two, preferably exactly two legs (21) and a base (22) connecting the legs (21). The tools (10) comprise one or more of the following further elements: a handle (30) integrally connected to the clamp (20), wherein the handle (30) is connected to the base (22) of the clamp (20) via at least one first predetermined breaking point (91); a drilling aid (40) having at least two openings (41) whose distance (D) is greater than the distance (d) of the legs (21) of the clamp (20); a drill (50) which is connected, in particular at a first end (51), to the handle (30) via at least one third predetermined breaking point (93); a separation opening (42) which is designed in such a way that, in particular after separation of the drilling aid (40) from the handle (30), the clamp can be received in the separation opening (42), in particular in the region of the first predetermined breaking point (91), in such a way that the clamp (20) can be separated from the handle (30) at the first (Continued)

predetermined breaking point (91). More generally, there are also disclosed one-piece surgical tools (10; 10') having at least two elements interconnected by predetermined breaking points.

19 Claims, 9 Drawing Sheets

(51) Int. Cl.
  *A61B 17/10* (2006.01)
  *A61B 17/17* (2006.01)
  *A61B 90/00* (2016.01)
(52) U.S. Cl.
  CPC .............. *A61B 90/03* (2016.02); *A61B 90/06* (2016.02); *A61B 2017/00526* (2013.01); *A61B 2090/037* (2016.02); *A61B 2090/061* (2016.02)

(56) References Cited

U.S. PATENT DOCUMENTS

| | | | | |
|---|---|---|---|---|
| 5,902,310 | A * | 5/1999 | Foerster | A61B 90/39 606/151 |
| 7,458,494 | B2 * | 12/2008 | Matsutani | A61B 34/76 227/19 |
| 8,584,853 | B2 * | 11/2013 | Knight | A61B 50/30 206/439 |
| 11,090,095 | B2 * | 8/2021 | Knight | A61B 17/0642 |
| 2005/0256537 | A1 * | 11/2005 | Cummins | A61B 17/0684 606/219 |
| 2012/0228355 | A1 * | 9/2012 | Combrowski | A61B 17/0642 227/175.1 |
| 2016/0242863 | A1 | 8/2016 | Kirschman | |
| 2017/0296174 | A1 * | 10/2017 | Wahl | A61B 50/33 |

FOREIGN PATENT DOCUMENTS

| | | |
|---|---|---|
| DE | 10309490 B3 | 9/2004 |
| DE | 69918068 | 10/2004 |
| EP | 2106754 B1 | 10/2009 |
| EP | 2474271 B1 | 7/2012 |
| WO | 2004004578 A1 | 1/2004 |
| WO | 2020260470 A1 | 12/2020 |

OTHER PUBLICATIONS

European Search Report for European Application No. 19183164.3 dated Feb. 21, 2020, 32 pages.

"Medical & Survival Cards with Hooks, Lock Picks, Saws & More—Readyman", Retrieved from the Internet: https://www.readyman.com/collections/survival-cards/products/readyman-total-survival-kit [retrieved Dec. 22, 2021] 14 pages.

* cited by examiner

SURGICAL TOOL AND SURGICAL SET

The present invention relates to surgical tools according to the preambles of the independent patent claims and to surgical sets. Tools are known which are provided with clamps which can find use in bone surgery, in particular for compressing bones or fragments thereof.

EP 2 106 754 A1 discloses surgical instruments with a clamp and two handles which are connected to the clamp via predetermined breaking points. Openings are provided in the handles to accommodate a tool. This allows the clamp to be bent open or closed.

WO 2004/004578 A1 discloses tools having a clamp and a retaining part connected to the clamp by weakened tabs.

The instruments disclosed in EP 2 474 271 A2 have retaining parts which are connected to a clamp via recessed predetermined breaking points. The predetermined breaking points are located in a corner area between the legs and the base of the clamp. Template holes and recesses are provided in the retaining part.

Furthermore, DE 198 59 950 A1 discloses a clamp arranged within a recess of a material sheet.

However, the surgical tools known from this prior art have a number of disadvantages. For example, when the staples disclosed in EP 2 474 271 A2 are cut off, sharp-edged contours may be produced which can cause damage to the body tissue when the staple is inserted. Furthermore, in many cases, the use of the staples requires additional tools for drilling holes, cutting and insertion, which must be individually adapted to the staples, making them difficult to provide.

It is therefore an object of the present invention to provide surgical tools with surgical clamps in which the above-mentioned disadvantages are eliminated or at least reduced. In particular, the clamps should cause as little damage as possible to the body tissue, and the provision of further tools required for the use of the clamps should be simplified as much as possible.

In a first aspect, the invention relates to a surgical tool comprising a surgical clamp and a handle. The clamp has at least two, preferably exactly two legs and a base connecting the legs. The handle is integrally connected to the clamp. According to the first aspect of the invention, the handle is connected to the base of the clamp via at least one first predetermined breaking point. Due to the arrangement of the first predetermined breaking point at the base of the staple, no sharp edges are formed at the legs of the staple during separation. This protects the body tissue postoperatively.

A predetermined breaking point is understood here and in the following to be a point on the tool which connects a first part of the tool (for example the handle) with a second part of the tool (for example with the clamp), whereby this connection can be separated specifically at this point by applying a breaking torque. In this case, the breaking torque can be in the range of 0.1 Nm to 2 Nm. The predetermined breaking point can be formed, for example, by a point on the tool which is thinner than adjacent areas of the tool.

Preferably, the tool further comprises a drilling aid having at least one opening that can be connected to the handle, in particular via at least a second predetermined breaking point. By separating the drilling aid at the second predetermined breaking point, the drilling aid can be used to precisely position at least one hole in an area of a bone in which the staple is to be inserted. The drilling aid is indirectly connected to the clamp via the handle. This ensures that a drilling aid matched to the clamp is immediately available and does not have to be provided separately.

A second aspect of the invention relates to a surgical tool comprising a surgical clamp and a drilling aid. The surgical clamp has at least two, preferably exactly two legs and a base connecting the legs. In particular, it may be a surgical tool according to the first aspect of the invention. According to the second aspect of the invention, the drilling aid comprises at least two openings whose distance is greater than the distance of the legs of the clamp. Such a drilling aid allows holes to be positioned in two or portions of a bone such that compression of the bone can be achieved using the clamp. When the legs are inserted into the holes, the bone is compressed between the areas.

Also, a third aspect of the invention relates to a surgical tool having a surgical clamp and a handle, wherein the clamp has at least two, preferably exactly two legs and a base connecting the legs, and the handle is connected to the clamp, in particular integrally. For example, it may be a tool as described above. According to the third aspect of the invention, the tool further comprises at least one drill connected to the handle via at least a third predetermined breaking point. In particular, the drill may be connected to the handle at a first end via the third predetermined breaking point. Such a tool opens up the possibility of directly providing, together with the staple, a drill adapted to the staple for making a hole in a bone into which a leg of the staple can be inserted.

In preferred embodiments, the drill has a first drill tip at the first end and the third predetermined breaking point is spaced from the first drill tip. The third predetermined breaking point can preferably be arranged adjacent to a transition region between a shank of the drill and a conical section at the first end. In this way, the drill tip is prevented from being damaged when the drill is cut off at the third predetermined breaking point.

It is further advantageous if the drill is connected at a second end via at least a fourth predetermined breaking point to a drilling aid (in particular to a drilling aid as described above), which is part of the tool, has at least one opening and is connected to the handle via at least a second predetermined breaking point. By means of the drilling aid, the advantages explained above can be achieved.

In advantageous embodiments, the drill has a second drill tip at the second end and the fourth predetermined breaking point is spaced from the second drill tip in a similar manner as the third predetermined breaking point is spaced from the first drill tip. In this regard, in one variation, it is conceivable that the first and second drill tips are of different dimensions, for example, to selectively drill holes of one of two different diameters. In a second variant, the first and second drill tips can also be of the same dimensions, whereby a diameter is clearly specified.

Furthermore, it is preferred if the handle has at least one clamp receptacle in which the clamp separated from the handle can be inserted in a force-fitting and/or form-fitting manner. Thus, after separating the handle from the clamp, it is possible to hold the clamp with the aid of the handle. No separate tool is therefore required for this.

In one possible embodiment, the clamp receptacle is formed as a recess formed at a first end of the handle. This represents a structurally simple, yet effective design.

In a fourth aspect, the present application also relates to a surgical tool comprising a surgical clamp, a handle and a drilling aid, wherein the tool may again be as described above. Here, the clamp has at least two, preferably exactly two legs and a base connecting the legs. The handle is integrally connected to the clamp via at least one first predetermined breaking point, and the drilling aid has at least one opening which is connected to the handle, in particular via at least one second predetermined breaking point. According to the fourth aspect, the tool and in particular the drilling aid comprises at least one separation opening which is configured such that, in particular after separation of the drilling aid from the handle, the clamp, when still connected to the handle, can be received in the separation opening, in particular in the region of the first predetermined breaking point, such that the clamp can be separated from the handle at the first predetermined breaking point. The separation opening can also be arranged in another area of the tool, which can be separated from the handle for the staple and the staple. Thus, the tool directly provides the possibility to separate the clamp from the handle. This is particularly advantageous if the bone to be treated is so unstable that it is not possible to separate the handle when the staple is already implanted. The use of the integrated cut-off hole also reduces the risk of destroyed surgical gloves, which can be present with purely manual bending. This also does not require a separate tool, which must be selected and additionally provided.

It is further expedient if the drilling aid has a bending region which is arranged between an opening region containing the opening for receiving a drill and a slot region containing the separation opening and which allows the drilling aid to be bent. In this way, the drilling aid can be bent as required to facilitate access to the bone to be treated or to enable access in the first place.

It is also advantageous if the first predetermined breaking point is recessed relative to a boundary surface of the base facing the handle. This design has the effect that any sharp edges that arise when the retaining part is separated are also recessed with respect to the boundary surface of the base. As a result, no sharp edges are formed on the base of the clamp when it is separated, and this also applies to the side of the base facing away from the legs. This contributes to further protection of the body tissue.

Further advantages arise if the drilling aid comprises an impact notch for driving the staple separated from the handle into a bone, the impact notch preferably being arranged at a second end of the handle opposite the staple receptacle.

More generally, the invention also relates to one-piece surgical tools comprising at least two elements interconnected at least partially by predetermined breaking points and/or predetermined bending points, wherein at least one of the elements, preferably at least two of the elements, is/are selected from the following list:

at least one surgical staple having at least two, preferably exactly two legs and a base connecting the legs;
at least one surgical drill;
at least one surgical scalpel;
at least one surgical wand, with which, for example, the depth of a hole drilled in a bone can be measured;
at least one scale;
at least one surgical sliding aid, in particular for inserting a surgical wand;
at least one component, in particular a blank for at least one arm or a part of a blank for at least one arm, of surgical forceps;
at least one component, in particular a blank for a handle or a part of a blank for at least one handle, of a surgical screwdriver or a surgical scalpel;
at least one surgical K-wire.

The latter tools also include, for example, tools which together form a blank for an arm of surgical forceps or a blank for a handle of a surgical screwdriver or a surgical scalpel, the blank comprising at least two elements or parts which are connected to one another via a predetermined bending point at which the blank can be bent in order to obtain an arm of forceps or a handle of a screwdriver or scalpel, respectively.

Further aspects of the invention relate to surgical tools, which can be provided on the basis of blanks made from metal sheets. These tools can be used as individual tools and preferably in combination with the tools and blanks described above.

For example, flat blanks can be used to provide compression forceps for K-wires or forceps for a distraction.

To provide such forceps, two flat blanks are proposed. One of these blanks can preferably be provided with a pressed pin. By bending, the two blanks can be formed into a shape such that they form two arms of a pair of forceps when assembled. Accordingly, this aspect relates to a set of two blanks which are bendable and pivotally connectable to each other at a pivot point such that the pivotally assembled bent blanks form two arms of a pair of forceps. The bending may be accomplished at a predetermined bending point mentioned above.

It is further conceivable to also produce a K-wire from a sheet, in particular by three-dimensional laser cutting or additional processing steps such as milling or grinding. In particular, such a K-wire can have an optimized tip. The K-wire can also be designed as a triangular K-wire.

Another possible application relates to a blank which can be used to produce a handle, for example for a screwdriver or for a scalpel. The blank has at least two, preferably three, arms for forming side faces. The side faces can be bent to form a handle. In this case, the side surfaces are connected to one another at a rear end by means of a connecting region and are provided at a front end with contours which, preferably by bending over, form an interface for the insertion of screwdriver blades, in particular for AO, dental, Stryker or similar attachments or scalpel blades. The bending can be carried out at a predetermined bending point mentioned above.

It is also conceivable to provide a temporary plate fixer (a so-called olive K-wire) as a blank from a sheet.

While the latter various tools can also be used advantageously on their own, it goes without saying that combinations with other tools or components are also preferably conceivable. The provision of blanks made of sheet metal allows individual tools or components to be flexibly combined with one another depending on the desired application.

These tools also preferably have at least one handle, e.g. for holding a surgical object, in particular a surgical clamp and/or at least one surgical drilling aid with at least one opening.

The elements of the tool are preferably matched to each other. The one-piece connection enables a loss-proof and error-free provision of several such matched elements.

The surgical tools according to the invention can be made, for example, of a metal such as steel or of titanium, plastic, nitinol or ceramic. They can be made, for example, by mechanical punching, laser cutting, milling, water jet cutting or eroding from a sheet metal or by mechanical processing (for example, milling, drilling or grinding) and bending, embossing or pressing. The sheet metal may have a thickness in the range of 0.1 mm to 8 mm. The legs of the clamp have a thickness of 0.1 mm to 8 mm and may be spaced from each other by a distance ranging from 2 mm to 40 mm, preferably from 8 mm to 10 mm.

A further aspect of the invention relates to a surgical set comprising at least one surgical tool as described above a package in which the tool is sterilely packaged. In particular, in the context of the present invention, the tool is referred to as being sterilely packaged if it complies with at least one, preferably all, of the standards DIN EN ISO 11137, DIN EN 556, and DIN EN ISO 11607. The sterilization can be carried out, for example, thermally (such as by steam sterilization, hot air sterilization or fractional sterilization), chemically (such as by wet antiseptic, dry antiseptic) or physically (such as by high-pressure sterilization, radiation sterilization, for example with UV, X-ray, gamma radiation or electron bombardment, plasma sterilization or sterile filtration).

The invention is explained in detail below with reference to an example of an embodiment. Thereby shows FIG. 1: a first surgical tool according to the invention in a top view;

FIG. 2: a second surgical tool according to the invention in a perspective view;

FIG. 3: an alternative embodiment of the tool from FIG. 1;

FIG. 4: an enlarged view of a section A of FIG. 1;

FIG. 5: an enlarged view of a section B of FIG. 1;

FIG. 6a: a first part of compression forceps for K-wires (uncoiled on the left and bent on the right);

FIG. 6b: a second part of compression forceps for K-wires (uncoiled on the left and bent on the right);

FIG. 6c: a compression tong assembled from the parts shown in FIGS. 6a and 6b;

FIG. 6d: a K-wire;

FIG. 7: an alternative embodiment of compression forceps;

FIG. 8a: a blank for the manufacture of a screwdriver handle;

FIG. 8b: the blank from FIG. 8a with bent ends;

FIG. 8c: the blank from FIG. 8a bent into an open handle;

FIG. 8d: the handle from FIG. 8c with the screwdriver blade inserted;

FIG. 8e: the screwdriver from FIG. 8d with closed handle;

FIG. 8f: a perspective view of the interface between the screwdriver and the screwdriver handle of Figure e, and FIG. 9: a temporary plate fixator ("olive K-wire").

The first surgical tool 10 according to the invention shown in FIG. 1 comprises a surgical clamp 20 with two legs 21 and a base 22 connecting the legs. A handle 30 is connected to the base 22 via two predetermined breaking points 91. The first predetermined breaking points 91 are recessed with respect to a boundary surface of the base 22 facing the handle 30.

The tool 10 further comprises a drilling aid 40 with two openings 41. The drilling aid 40 is connected to the handle 30 via a second predetermined breaking point 92. The openings 41 of the drilling aid have a distance D which is greater than the distance d of the legs 21 of the clamp 20. Furthermore, in this embodiment, the drilling aid 40 of the tool 10 has a separation opening in the form of two separation slots 42. In alternative embodiments according to the invention, a separation opening could also be formed in another element of the one-piece tool 10. The drilling aid 40 further comprises a bending region 44 disposed between an opening region 45 containing the openings 41 and a slot region 46 containing the separation opening. The drilling aid 40 further comprises an impact notch 43 for impacting the clamp 20 separated from the handle 30 into a bone. The impact notch 43 is arranged at a second end 33 of the handle 30 opposite a staple receiving portion 31. The functions of the separation slot 42, the bending portion 44, and the impact notch 43 will be explained in further detail below.

The tool 10 further includes two drills 50 that are connected to the handle 30 at respective first ends 51 via third predetermined breaking points 93 (see also FIG. 5). The drills 50 have a respective first drill tip 53 at their ends 51, the third predetermined breaking points 93 being spaced apart from the first drill tips 53. At their respective second ends 52, the drills 50 are connected to the drilling aid 40 via fourth predetermined breaking points 94. Also at their respective second ends 52, the drills 50 have a respective second drill tip 54, the fourth predetermined breaking points 94 being spaced from the second drill tips 54.

The clamp receptacle 31 is formed as a recess formed at a first end 32 of the handle 30. The function of the recess is also explained below.

To use the tool 10, the drilling aid 40 can be separated from the handle 30 at the second predetermined breaking point 92 in a first step. Preferably, the drills 50 are also separated from the handle 30 at the third predetermined breaking point 93, while they initially remain connected to the drilling aid 40 at the fourth predetermined breaking point 94. Alternatively, when separating the drilling aid 40 from the handle 30, the drills 50 can be separated from the drilling aid 40 at the fourth predetermined breaking points 94, while the drills 50 initially remain connected to the handle 30 via the third predetermined breaking points 93.

After the drilling aid 40 has thus been separated from the handle 30, the legs 21 of the clamp 20 still connected to the handle 30 can be inserted into the separation slots 42 so that the first predetermined breaking points 91 come to lie adjacent to the separation slots 42. By bending the handle 30 and the clamp 20 still connected thereto, the clamp 20 can be separated from the handle 30 at the first predetermined breaking points 91 in a clean and controlled manner. Due to the arrangement of the predetermined breaking points 91 at the base 22, sharp breaking edges occur at most on the sides facing away from the legs 21.

Before or after separating the clamp 20 from the handle 30, the drill aid 40 may be used in a manner known per se to define the positions of two holes in two regions of a bone (e.g., over a fracture or in two bones over a joint to be fused). If necessary, the drill guide 40 can be bent in the tapered bending region 44 to allow accessibility. The holes can be made using the drills 50 separated from the handle 30 and the drill aid 40.

The clamp 20 separated from the handle 30 can then be clamped with its base in the recess 31 of the handle 30 and thus held in a force-fit and/or form-fit manner. The recess 31 serves as an anti-slip device when tapping in. The two legs 21 of the clamp can then be inserted into the holes made in the bone. The drive-in notch 43 allows the clamp 20 to be driven carefully into the bone, bringing it even closer to the bone.

FIG. 2 shows a second surgical tool 10' according to the invention, which is also formed in one piece. It contains the following elements, which are connected to each other via predetermined breaking points 95:

a surgical drilling aid 140 with two openings 141;
a surgical scalpel 60 having a blade 61;
a sliding aid 80 with two openings 81;
a scale 71;
a wand 70.

The drilling aid 140 includes a handle 145 and a tab 141 connected thereto. The tab 141 includes a central portion 142 from which a rectangle 143 projects laterally, and two end portions 144, each of which includes one of the apertures 141. For use, the rectangle 143 and the end regions 144 are each folded 90° to the same side. The protruding rectangle 143 is used as a stop for the end regions 144. Thus, the two openings 141 are axially aligned facing each other. A drill can then be pushed axially through both openings 141 and guided in this way.

The sliding aid 80 has a handle 85 and a tab 81 connected thereto. The tab 81 contains a central area 82 and two end areas 84, each of which contains one of the openings 81. For use, the end portions 84 are each folded 90° to the same side. Thus, the two openings 81 are axially aligned opposite each other. The wand 70 is then slid through the aligned apertures 81. To measure the depth of a hole drilled in a bone, the wand 70 is slid into the hole. Then the sliding aid 80 is slid to the stop. The construct is thus held, pulled out of the hole and held against a scale 71 arranged on the tool 10' and read. In this way, the depth of the hole can be determined.

The tool 10' may be designed for one or more specific indications and have the necessary and suitable elements for this purpose, which can be separated and used by cutting them off at the predetermined breaking points.

FIG. 3 shows an alternative embodiment of the tool from FIG. 1. The differences compared to the embodiment according to FIG. 1 are explained below. Instead of two separation slots, only one separation slot 42 is provided, which has a width that corresponds approximately to the width of the clamp 20. Furthermore, the clamp 20 has a beveled base 22 which runs at an angle α of approximately 25°.

FIG. 4 shows an enlarged view of section A of FIG. 1. The predetermined breaking points 91 are recessed in a recess 24 in the base 22 on the side 23 facing the handle.

FIG. 5 shows an enlarged view of the section B of FIG. 1. The drills 50 have a shank 55 and a wedge-shaped section 56 at the first end 51. The wedge-shaped section 56 runs from the shank 55 into the drill tip 53. The predetermined breaking points 93 are arranged at a distance from the drill tip 53, adjacent to the transition between the shank 55 and the conical section 56. This arrangement of the predetermined breaking points 93 is advantageous, since an arrangement in the shank 55 would produce a larger hole due to burrs, and an arrangement at the tip would lead to running of the drill 50.

FIGS. 6a and 6b show a first arm 101 and a second arm 102 for a compression clamp 100 (see FIG. 6c). In each of FIGS. 6a and 6b, a flat blank is shown on the left side and a curved shape of the blank is shown on the right side.

The first arm 101 has a pin 103 pressed to the blank 101. The blank 101 also has a recess 105 for receiving the bent second arm 102 (see FIG. 6c). Furthermore, openings 106 are provided for receiving a K-wire. The blank for the first arm 101 is bent along a central axis M to form a U-shaped cross-section. The blank may be provided flat or in a pre-bent form. Similarly, the pin 103 may be provided pre-bent, separately or as a separable part on the tool 10.

FIG. 6b shows a blank for the second arm 102. The second arm 102 is provided with two openings 104 through which the pin 103 can be guided. Openings 106 are also provided in the second arm. The second arm is also bent (see FIG. 6b, right) along a central axis M to form a U-shaped cross-section. By assembling the first arm 101 and the second arm 102, the compression forceps 100 shown in FIG. 6c are formed. To do this, the second arm 102 is inserted through the recess 105 and placed on the pin 103.

FIG. 6d shows a K-wire 107. The K-wire 107 is cut out of a sheet by 3D laser cutting or produced by additional milling, grinding or pressing of a laser-cut part. Three-dimensional tips 108 can be formed at the same time.

FIG. 7 shows an alternative embodiment of a compression forceps 110, which is constructed from a first arm 111 and a second arm 112. The first arm 111 and the second arm 112 are pivotally connected to each other via a pin 113, which is pressed or bent out and countersunk into the first arm 112. The first arm 111 and the second arm 112 are both fabricated as flat blanks from a sheet metal. The second arm 111 has a guide track 115 along which a stop 114 of the second arm 112 can be guided. The first arm 111 and the second arm 112 have bent sections 118 which form a handle. A compression head 117 is formed at an end remote from the handle 118. The compression head 117 includes apertures 116 and slot-shaped apertures 119. The slot-shaped openings 119 (similar to slot-shaped openings 119 in the area of the handle 118) serve to facilitate bending.

FIGS. 8a to 8f show various configurations of a handle 120 for a screwdriver. The handle 120 is formed from a flat blank. FIG. 8a shows the flat blank for the handle 120. The blank has a connecting region 122 from which three arms 121 extend in a star shape. Slots between the connecting region 122 and the arms 121 facilitate bendability. End regions 123a, 123b and 123c are arranged at the ends of the arms 121, which form an interface in the assembled handle 120 for receiving a blade 125 (see FIG. 8f).

FIG. 8b shows the blank from FIG. 8a with individual, bent elements in the area of the end regions 123a, 123b and 123c.

To form the handle 120, the arms 121 are bent by 90° so that a three-dimensional body is formed (see FIG. 8c). An interface 124 for the blade 125 is formed by the bent parts in the end regions 123a, 123b and 123c. A guide opening 129 is used to receive the shank of the blade 125. An anti-rotation opening 127 is used to receive an out-of-round portion of the blade 125 for transmitting torque. An end stop 128 defines an axial end position for the blade 125. Two inwardly directed projections form an axial retainer 126, in which the blade 125 can positively engage with a constriction.

FIG. 8d shows the handle 120 with the blade 125 inserted. After inserting the blade, the last arm (here the arm with the end piece 123a) is bent into an end position so that the axial securing device 126 engages in the recess on the blade 125 (see FIG. 8e).

Figure 1:
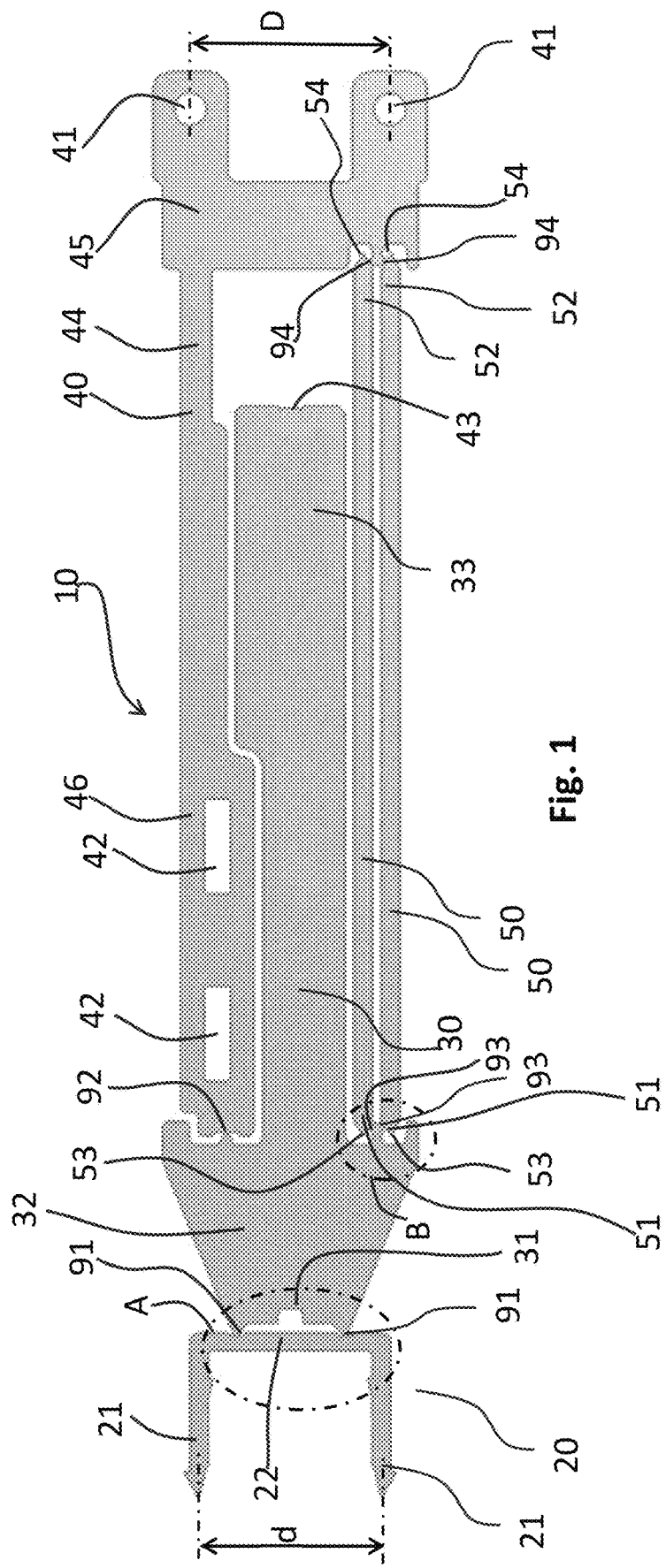
Figure 2:
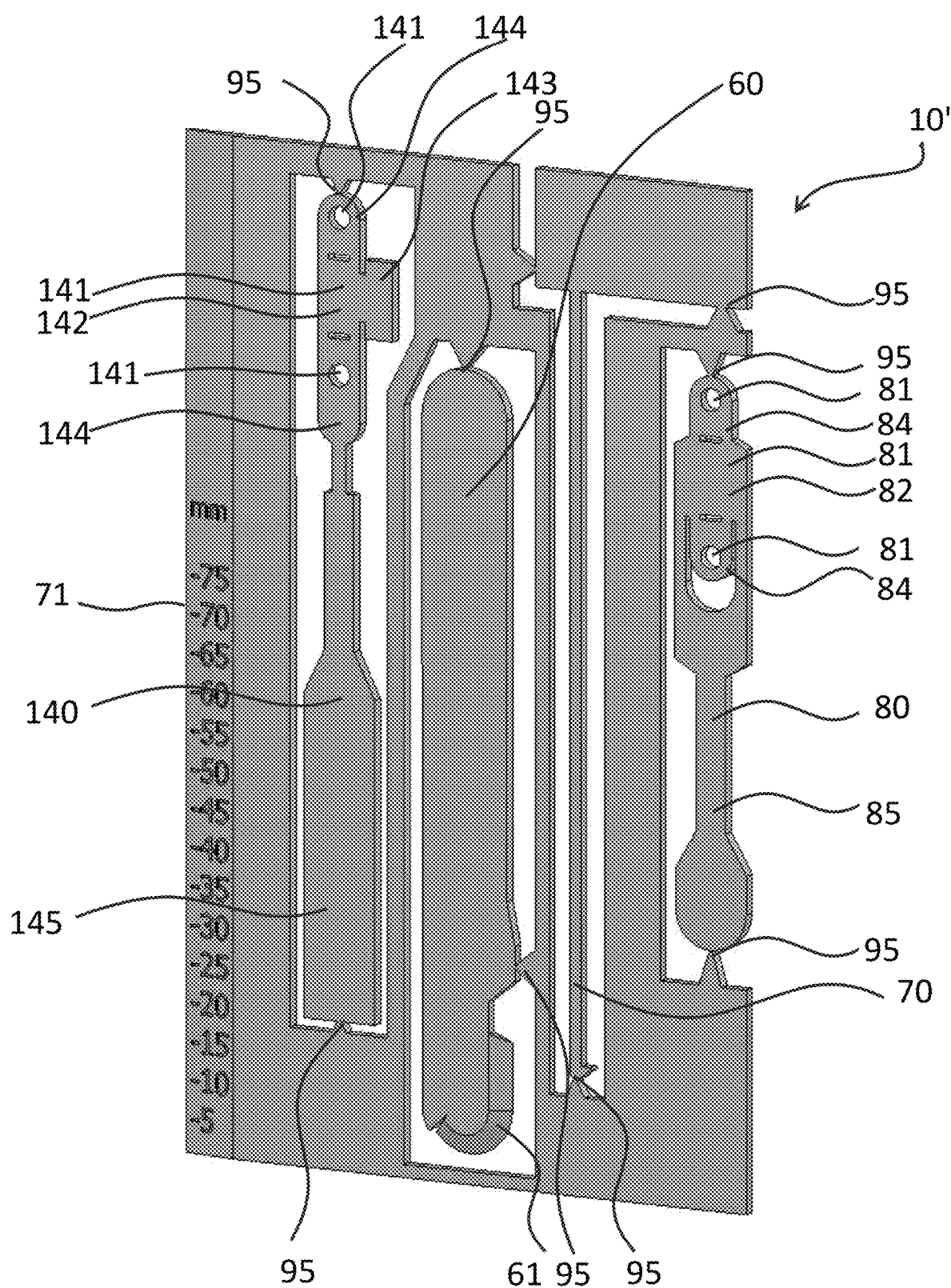
Figure 3:
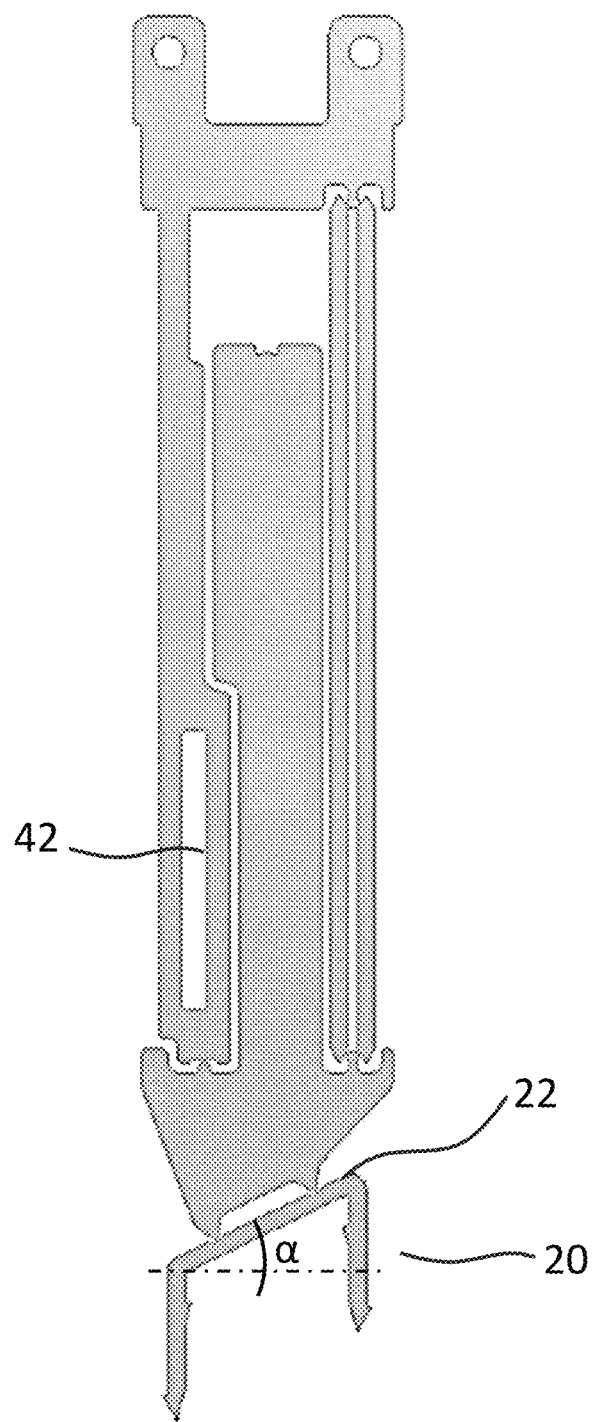
Figure 4:
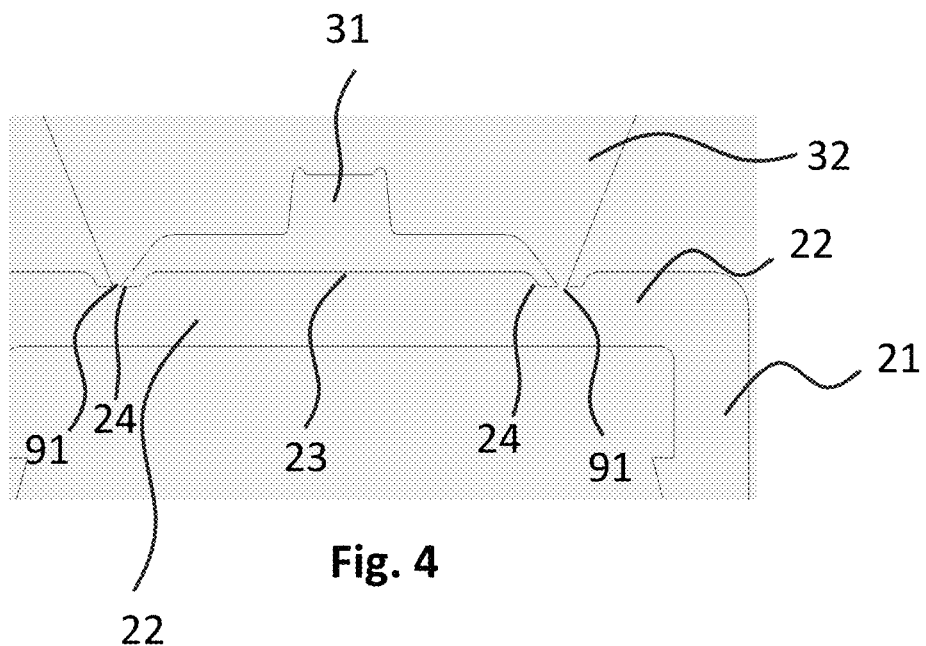
Figure 5:
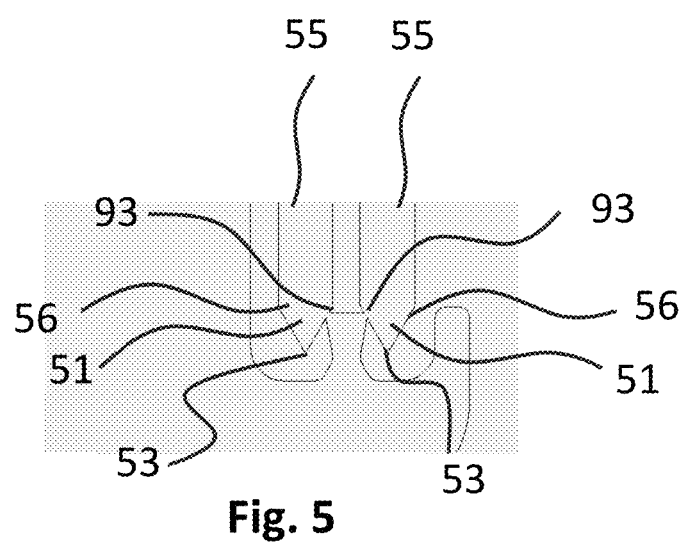
Figure 6A:
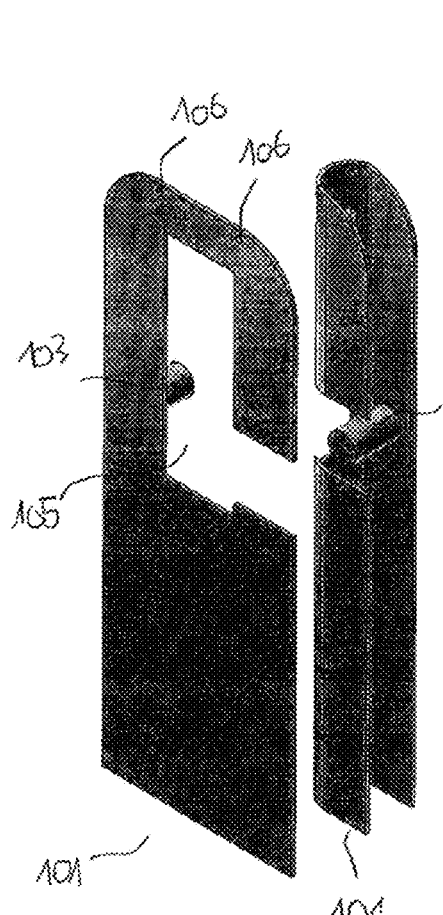
Figure 6B:
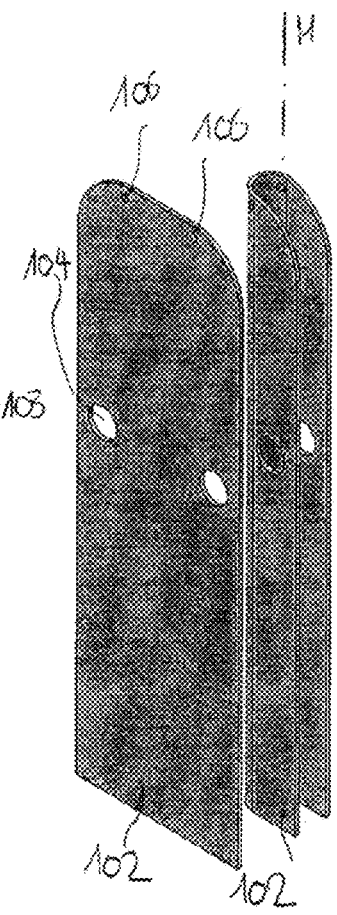
Figure 6C:
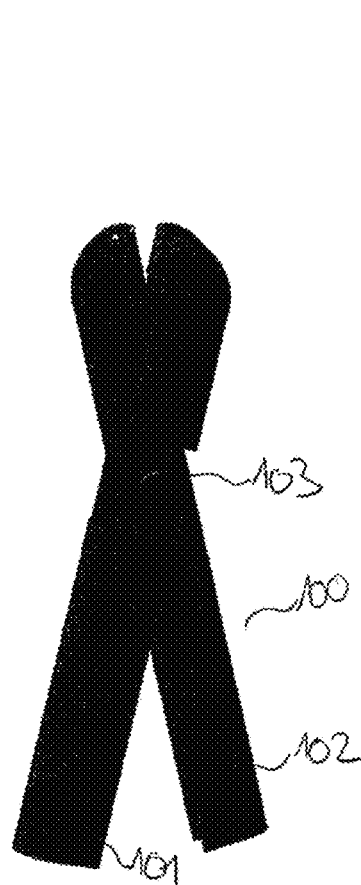
Figure 6D:
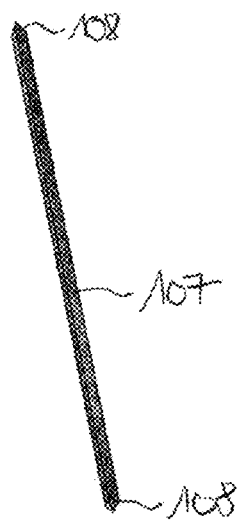
Figure 7:
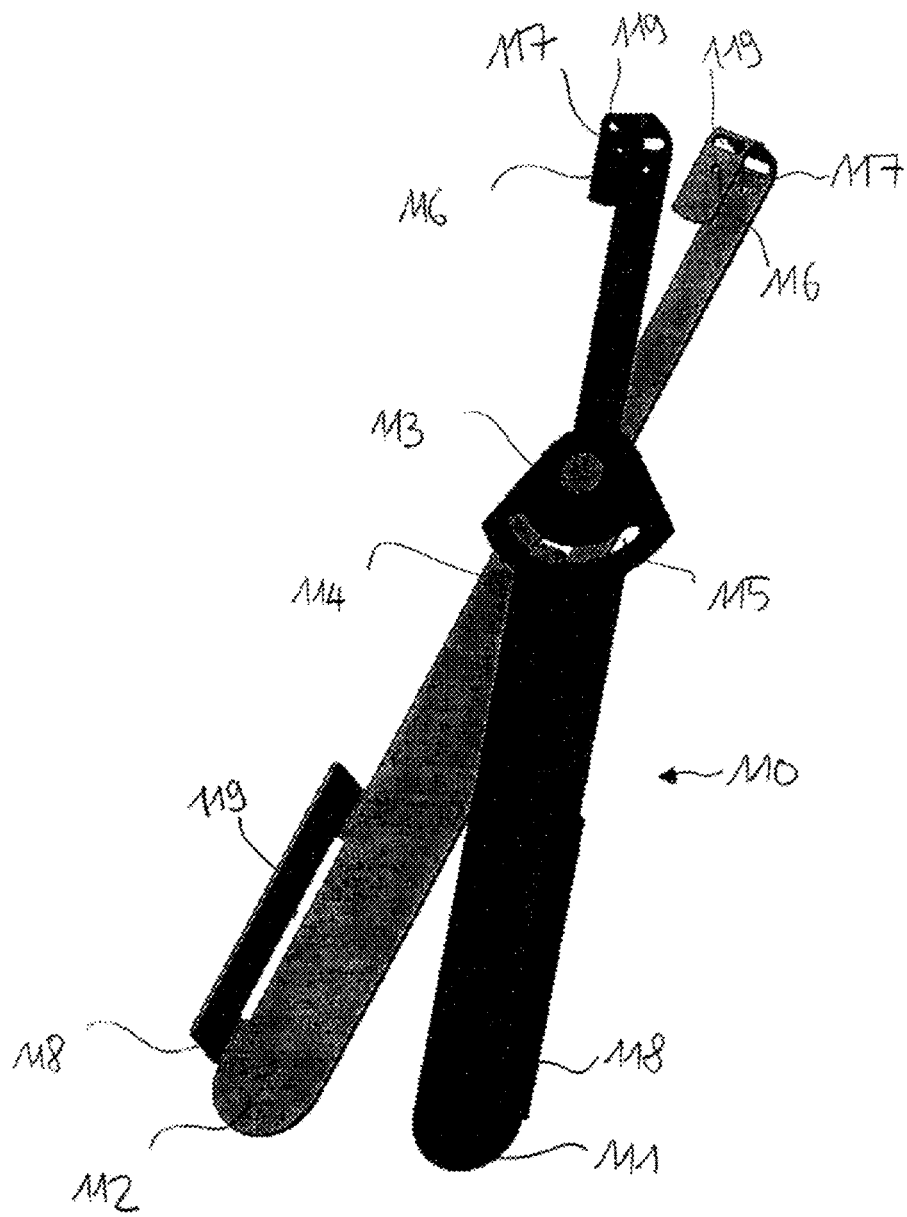
Figure 8A:
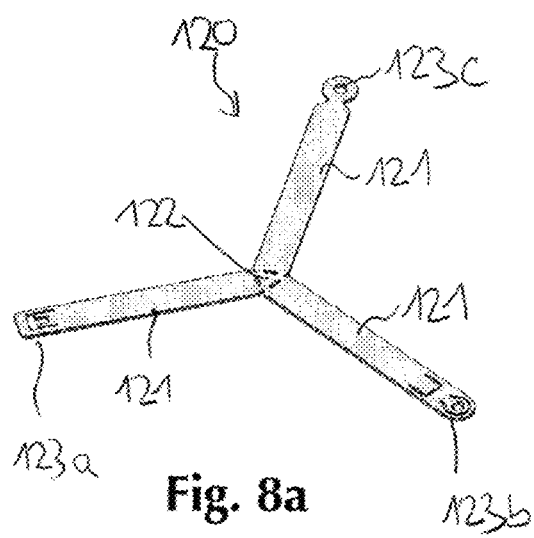
FIG. 8f shows an enlarged view of the interface 124 for receiving the blade 125.
Figure 8B:
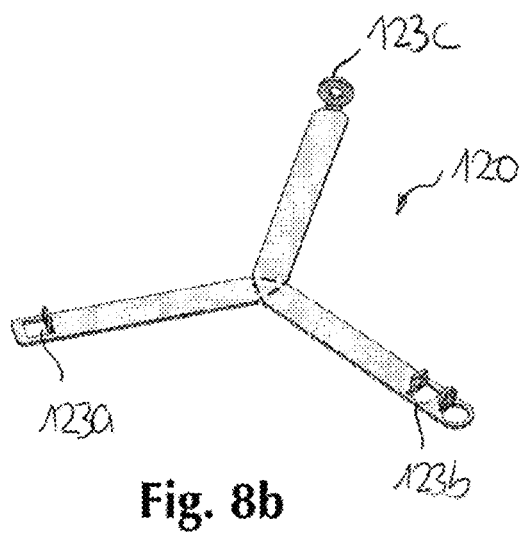
Figure 8C:
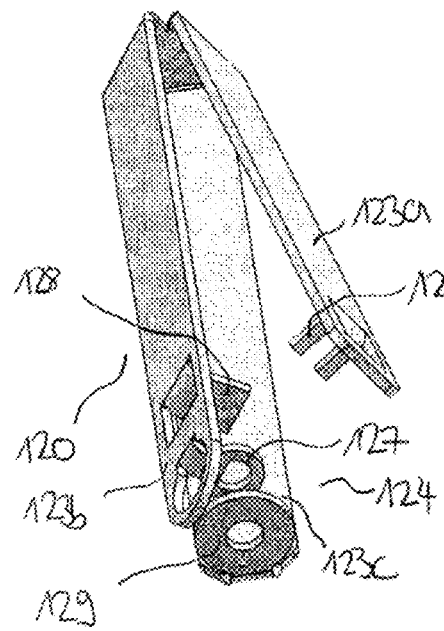
Figure 8D:
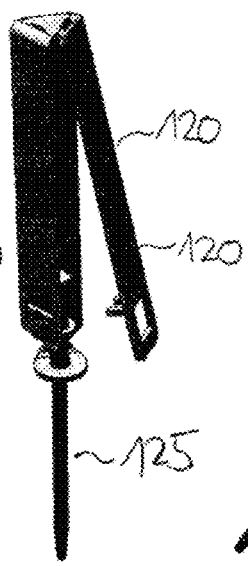
Figure 8E:
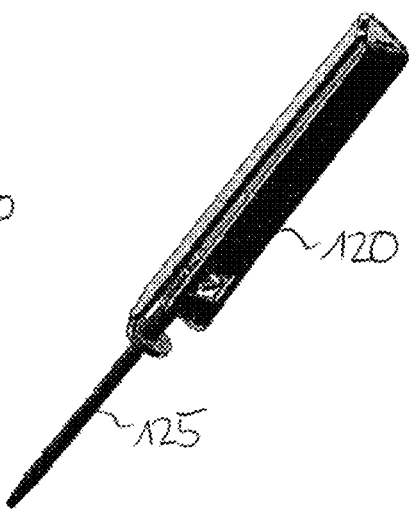
Figure 8F:
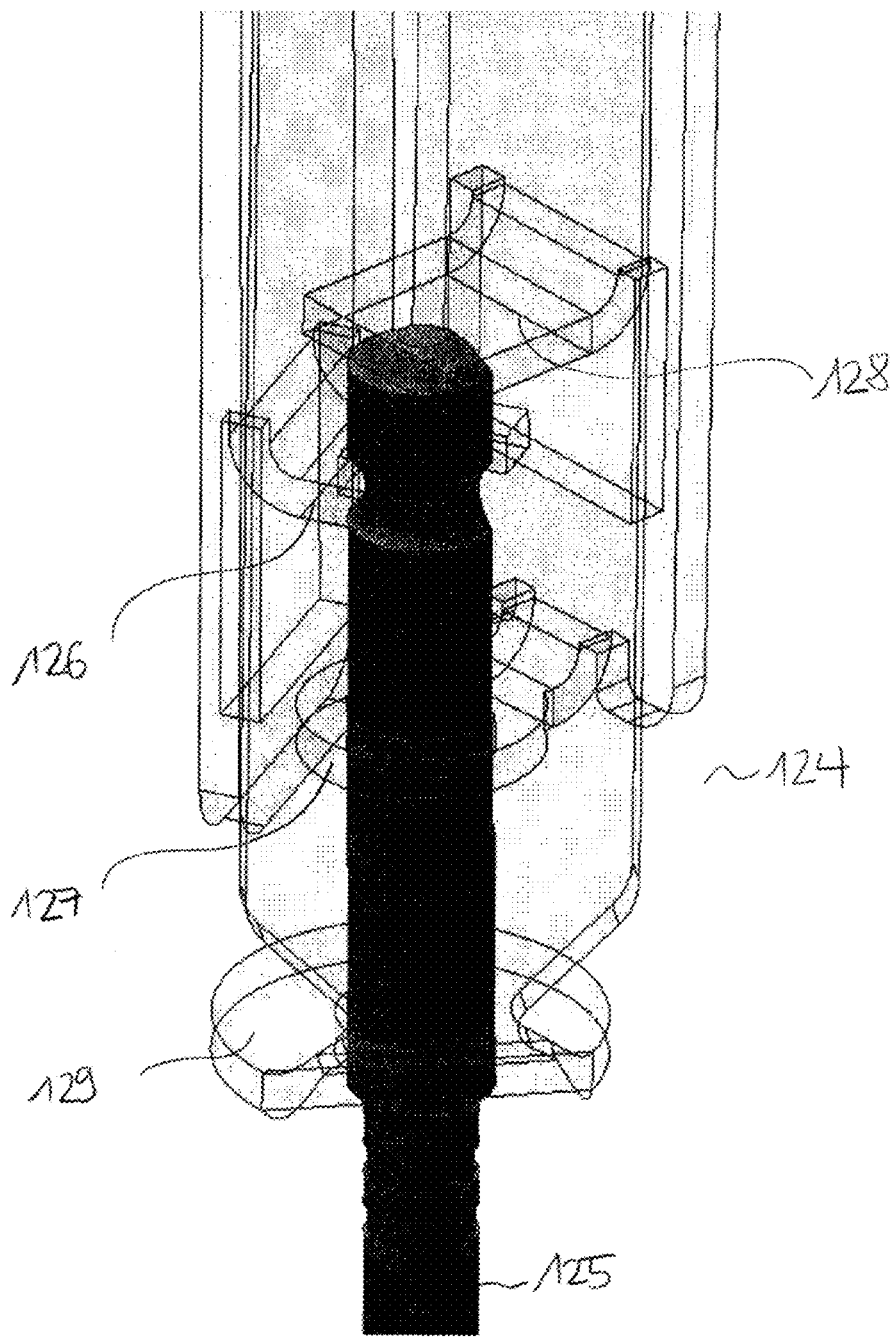
Figure 9:
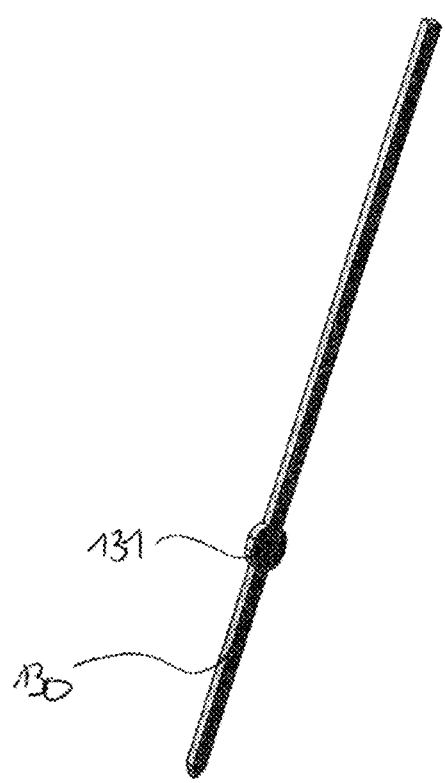
FIG. 9 shows a temporary plate fixer ("olive K-wire") 130. The temporary plate fixator 130 has the shape of a K-wire with an olive 131.

The invention claimed is:

1. A surgical tool, comprising:
   a surgical staple having at least two legs and a base connecting the legs,
   a handle integrally connected to the staple,
   wherein the handle is connected to the base of the staple via at least a first predetermined breaking point,
   wherein the surgical tool comprises at least one further element selected from the group consisting of
   a drilling aid,
   a drill,
   a surgical scalpel,
   a surgical wand,
   a scale,
   a surgical sliding aid for inserting the surgical wand,
   a component of a surgical forceps,
   a component of a surgical screwdriver or a surgical scalpel, and
   a surgical K-wire, wherein the at least one further element is connected to the handle via at least one further predetermined breaking point.

2. The surgical tool according to claim 1, wherein the tool comprises the drilling aid with at least one opening, wherein the drilling aid is connected to the handle.

3. The surgical tool according to claim 2, wherein the drilling aid is connected to the handle via at least a second predetermined breaking point.

4. The surgical tool according to claim 1, wherein the drill is connected to the handle via at least one third predetermined breaking point, wherein the drill has a first drill tip at the first end and the third predetermined breaking point is spaced from the first drill tip.

5. The surgical tool according to claim 4, wherein the drill is connected at a second end via at least a fourth predetermined breaking point to a drilling aid.

6. The surgical tool according to claim 5, wherein the drilling aid has at least one opening and is connected via at least a second predetermined breaking point to the handle of the tool.

7. The surgical tool according to claim 5, wherein the drill has a second drill tip at the second end and the fourth predetermined breaking point is spaced from the second drill tip.

8. The surgical tool according to claim 1, wherein the handle has at least one staple receptacle in which the staple separated from the handle can be inserted in a force-fitting and/or form-fitting manner.

9. The surgical tool according to claim 8, wherein the staple receptacle is formed as a recess formed at a first end of the handle.

10. The surgical tool according to claim 1, wherein the first predetermined breaking point is recessed with respect to a boundary surface of the base facing the handle.

11. The surgical tool according to claim 1, wherein the drilling aid comprises an impact notch for impacting the staple separated from the handle into a bone.

12. The surgical tool according to claim 11, wherein the handle has at least one staple receptacle in which the staple separated from the handle can be inserted in a force-fitting and/or form-fitting manner the impact notch is arranged at a second end of the handle opposite the staple receptacle.

13. A surgical kit comprising at least one surgical tool according to claim 1 and a package in which the tool is sterilely packaged.

14. A one-piece surgical tool, containing
a surgical staple having at least two legs and a base connecting the legs,
a drilling aid,
interconnected at least partially by predetermined breaking points, wherein the drilling aid contains at least two openings whose distance is greater than the distance of the legs of the staple.

15. The surgical tool according to claim 14, wherein the surgical tool further comprises a handle integrally connected to the staple, wherein the drilling aid is connected to the handle.

16. A surgical tool, containing
a surgical staple having at least two legs and a base connecting the legs,
a handle connected to the staple,
wherein the tool further comprises at least one drill which is connected to the handle via at least one third predetermined breaking point,
wherein the handle is integrally connected to the staple via at least a first predetermined breaking point,
the surgical tool further containing a drilling aid with at least one opening which is connected to the handle,
wherein the tool further contains at least one separation opening which is designed in such a way that the staple is receivable in the separation opening in such a way that the staple is separable from the handle at the first predetermined breaking point.

17. The surgical tool according to claim 16, wherein the drilling aid is connected to the handle via at least one second predetermined breaking point.

18. The surgical tool according to claim 16, wherein the staple is receivable in the separation opening in the region of the first predetermined breaking point.

19. The surgical tool according to claim 16, wherein the drill aid comprises a bending portion disposed between an opening portion containing the opening and a slot portion containing the separation opening, the bending portion allowing the drill aid to be bent.

* * * * *